United States Patent

Untch et al.

[11] 4,033,978
[45] July 5, 1977

[54] THIACYCL[2.2.2]AZINE CARBOXYLIC ACIDS

[75] Inventors: Karl G. Untch, Los Altos; John O. Gardner, Palo Alto, both of Calif.

[73] Assignee: Syntex (U.S.A.) Inc., Palo Alto, Calif.

[22] Filed: Aug. 15, 1975

[21] Appl. No.: 604,983

Related U.S. Application Data

[62] Division of Ser. No. 499,713, Aug. 22, 1974, Pat. No. 3,920,672.

[52] U.S. Cl. .................. 260/306.7 R; 424/270
[51] Int. Cl.² ............................. C07D 513/16
[58] Field of Search ................... 260/306.7 R
[56] References Cited

UNITED STATES PATENTS 3,985,884  10/1976  Conrow et al. ............. 260/308 B

Primary Examiner—Donald G. Daus
Assistant Examiner—David E. Wheeler
Attorney, Agent, or Firm—Alan M. Krubiner; William B. Walker

[57] ABSTRACT

3-Carboxy-5-substituted-thiacycl[2.2.2]azines of the formula:

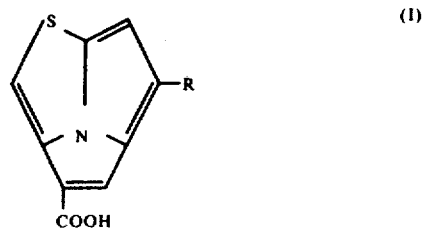

wherein R is phenyl or phenyl monosubstituted in the meta or para position with fluoro, chloro, lower alkyl of from 1 to 4 carbon atoms or lower alkoxy of from 1 to 4 carbon atoms, and the pharmaceutically acceptable salts thereof.

These compounds are useful as anticomplimentary agents, specifically for the treatment of inflammatory conditions, auto-immune diseases, allergic reactions and vascular diseases.

6 Claims, No Drawings

THIACYCL[2.2.2]AZINE CARBOXYLIC ACIDS

This is a division of application Ser. No. 499,713 filed Aug. 22, 1974, now U.S. Pat. No. 3,920,672.

SUMMARY OF THE INVENTION

The present invention relates to novel chemical compounds having a thiacycl[2.2.2]azine skeleton. More particularly the compounds of the present invention are 3-carboxy-5-substituted-thiacycl[2.2.2]azines of the formula:

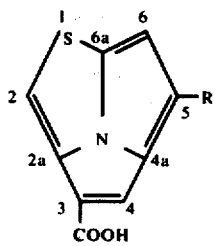

wherein R is phenyl or phenyl monosubstituted in the meta or para position with fluoro, chloro, lower alkyl of from 1 to 4 carbon atoms or lower alkoxy of from one to four carbon atoms, and the pharmaceutically acceptable salts thereof.

As used in the specification and the appended claims, unless specified to the contrary, the term "lower alkyl" refers to a straight or branched chain monovalent substituent consisting solely of carbon and hydrogen containing no unsaturation and having from 1 to 8 carbon atoms. The term "lower alkoxy" refers to the aforesaid lower alkyl group linked through an ether oxygen, and having its free valence from the ether oxygen. The term "lower alkylene" refers to a straight chain divalent substituent consisting solely of carbon and hydrogen containing no unsaturation and having its valences at the opposite ends of the carbon chain.

Examples of lower alkyl groups are methyl, ethyl, propyl, i-propyl, butyl, i-butyl, sec-butyl, tert-butyl, pentyl, i-pentyl, neopentyl, hexyl, heptyl, octyl, and the like. Examples of lower alkoxy groups are methoxy, ethoxy, propoxy, i-propoxy, butoxy, i-butoxy, sec-butoxy, tert-butoxy, pentyloxy, hexyloxy, octyloxy, and the like. Examples of lower alkylene groups are dimethylene, trimethylene, tetramethylene and the like.

The term "pharmaceutically acceptable salts" refers to salts derived from pharmaceutically acceptable non-toxic inorganic or organic bases. Salts derived from inorganic bases include the sodium, potassium, lithium, ammonium, calcium, magnesium, ferrous, zinc, manganous, aluminum, ferric and manganic salts, and the like. Salts derived from pharmaceutically acceptable organic non-toxic bases include salts of primary, secondary and tertiary amines, including naturally occuring amines, which amines may contain other functional groups such as hydroxy groups, amide linkages and the like. Exemplary of the organic amines which may be used for the preparation of the pharmaceutically acceptable salts of the compounds of the present invention are triethylamine, tripropylamine, 2-dimethylaminoethanol, 2-diethylaminoethanol, ethanolamine, lysine, arginine, histidine, caffeine, procaine, N-ethylpiperidine, hydrabamine, choline, betaine, ethylenediamine, glucosamine, methylglucamine, theobromine, purines, piperazines, piperidine and the like.

In the specification, including the preparations and examples as well as the claims, all reference to temperature is to degrees Centigrade.

The compounds of Formula I are useful as anticomplimentary agents. Accordingly, they are useful for the treatment of inflammatory conditions, auto-immune diseases such as glomerulonephritis, lupus erythematosus and rheumatoid arthritis; allergic reactions; and vascular diseases.

The compounds of Formula I can be made up in the form of conventional pharmaceutical preparations; for example, the aforesaid compounds can be mixed with organic or inorganic inert pharmaceutical carriers suitable for oral and parenteral administration in the form of solid, semi-solid, or liquid dosage forms such as for example, tablets, suppositories, pills, capsules, powders, liquid solutions, suspensions and the like, preferably in unit dosage forms suitable for administration of precise dosages. The pharmacuetical compositions containing the compounds of this invention may be subjected to the conventional pharmaceutical expedients such as sterilization and can contain conventional pharmaceutical excipients such as preservatives, stabilizing agents, emulsifying agents, salts for the adjustment of osmotic pressure or buffers. The compositions may also contain other therapeutically active materials. Actual methods of preparing such dosage forms are known or will be apparent to those skilled in the art. The composition to be administered will, in any event, contain a quantity of the above compound(s) in a pharmaceutically effective amount for relief of the particular condition being treated in accordance with the teachings of this invention.

The daily dosage regimen will necessarily be dependent upon the needs of the subject being treated and the judgment of the medical practitioner. Generally, a dosage of from about 0.1 to about 50 mg. of active compound of Formula I per kilogram of body weight per day will be utilized.

The compounds of formula I may be prepared by a multi-step process, starting with an appropriately substituted thiazole represented by the formula:

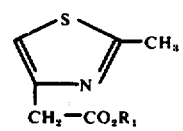

wherein $R_1$ is lower alkyl.

Thiazoles of this type, in particular wherein $R_1$ is ethyl, as well as the corresponding free acid are known. Such compounds may be prepared according to the methods of Steude (Ann, vol. 261, p. 22) and Arakawa (Chem. Pharm. Bull., vol. 20, p. 1041), for example, by reaction of the corresponding γ-bromoacetoacetate with thioacetamide.

In a first step, the thiazole ester of formula II is prepared for eventual fusion into a pyrrolo[2,1-b]thiazole by conversion to an N,N-disubstituted amide of the formula:

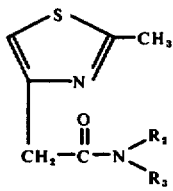

wherein $R_2$ and $R_3$ taken independently are each lower alkyl of from 1 to 3 carbon atoms, and $R_2$ and $R_3$ taken together are lower alkylene of from 4 to 6 carbon atoms, by reaction with an excess of a secondary amine of the formula $R_2R_3NH$, wherein $R_2$ and $R_3$ are as defined above. Suitable secondary amines that may be utilized include acyclic amines such as dimethylamine, diethylamine, methylethylamine, dipropylamine, methylpropylamine, ethylpropylamine, and so forth; as well as cyclic amines such as pyrrolidine, piperidine, and perhydroazepine. Preferred amines are low molecular weight acylic secondary amines such as dimethylamine and diethylamine. Dimethylamine is particularly preferred.

The amidation reaction is carried out according to methods known per se, such as for example by heating the ester of formula II with an excess of the secondary amine in a solvent medium. The reaction temperature should be between about 50° and 150°, preferably between about 80° and 120°. If a low molecular weight secondary amine such as dimethylamine or diethylamine is used, the reaction is preferably carried out in a sealed vessel, that is under pressure, to prevent substantial loss of the volatile secondary amine before reaction.

One may utilize an excess of the secondary amine as a solvent medium or preferably the excess amine is diluted with an additional solvent such as for example, a lower alkanol.

In the next step the amide of formula III is converted to a pyrrolo[2,1-b]thiazole of the formula:

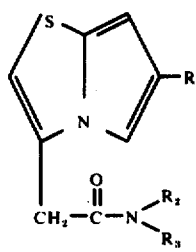

wherein, R, $R_2$ and $R_3$ are as above, in a two step procedure. In the first part of the procedure, the amide of formula III is intimately contacted with a phenacyl bromide of the formula:

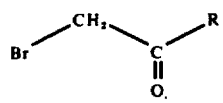

wherein R is as above.

Phenacyl bromides, as a class, are well known compounds. However, a particular phenacyl bromide useful in the present teaching which may not be known may be readily prepared from the appropriately substituted benzoic acid by conversion of said acid to its acid chloride, then conversion to the diazoketone by reaction with diazomethane, and finally conversion to the phenacyl bromide by reaction of the diazoketone with anhydrous hydrogen bromide, all according to methods known per se. Benzoic acid starting materials which may not be specifically known can be prepared in a variety of ways. For example, alkoxy substituted benzoic acids may be prepared by alkylation of hydroxybenzoic esters followed by saponification. Alkyl substituted benzoic acids may be prepared from e.g. alkylbromobenzenes by carbonation of the corresponding Grignard reagent.

The intimate mixing of the amide of formula III with the phenacyl bromide of formula IV results, initially, in the formation of a salt. This salt formation is effected by heating the intimate mixture of amide and phenacyl bromide to a temperature between about 60° and about 150°, preferably between 80° and 120°, preferably in the absence of any solvent.

The conversion of the salt thus formed to the pyrrolo[2,1-b]thiazole of formula IV is effected by treatment with a hydroxide base. Suitable hydroxide bases include alkali metal hydroxides such as sodium hydroxide, potassium hydroxide and lithium hydroxide, as well as quaternary ammonium hydroxides such as Triton B. A particularly preferred method involves the use of an ion exchange resin which has been rendered basic by pre-treatment with an alkali metal hydroxide. Suitable ion exchange resins include for example Amberlite CG-400 which has been pretreated with excess sodium hydroxide solution, and washed free of excess base.

The base treatment is preferably carried out at an elevated temperature, for example, from about 40° to about 80° preferably from about 50° to about 70°.

The reaction is performed in an inert organic solvent. Suitable inert organic solvents include lower alkanols such as methanol and ethanol. Methanol is particularly preferred. Both salt formation and base treatment are preferably performed in an inert atmosphere such as nitrogen or argon.

In the next step, the amide of formula V is converted to the free acid of the formula:

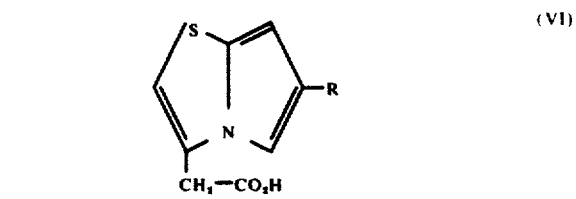

wherein R is as above.

This reaction is carried out under conditions normally employed for the hydrolysis of an amide to a carboxylic acid, for example, by heating with an alkali metal hydroxide in an aqueous alcoholic medium.

The carboxylic acid of formula VI is next esterified to afford the ester of the formula:

wherein R is as above and R₄ is methyl, ethyl or benzyl.

Esterification is carried out according to procedures known per se, such as for example, reaction of the carboxylic acid with the appropriate diazo compound such as for example, diazomethane, diazoethane or phenyldiazomethane, or reaction with the desired alcohol and trifluoroacetic anhydride.

In the next step the ester of formula VII is cyclized to afford a compound having a thiacycl[2.2.2]azine nucleus appropriately substituted as depicted in the formula

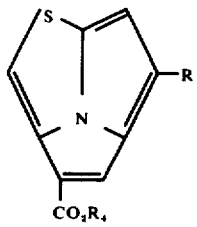

(VIII)

wherein R and R₄ are as above.

This conversion is accomplished by reaction of the ester of Formula VII with phosphorous oxychloride and dimethylformamide, at a reduced temperature, followed by treatment with an organic amine.

While the quantities of reagents utilized are not unduly critical, it is preferred to utilize a substantial excess of dimethylformamide over phosphorous oxychloride. The molar ratio of phosphorous oxychloride, relative to the compound of formula VII being cyclized, should be from about 1.0 to 1.5:1. The starting material of formula VII is generally present in a solvent medium prior to treatment with the phosphorous oxychloride-dimethylformamide reagent. A particularly preferred solvent medium is dimethylformamide itself.

The addition of the phosphorous oxychloride is effected as a mixture with dimethylformamide, said mixture being added containing an excess of dimethylformamide over the phosphorous oxychloride, preferably in a molar ratio of from about 1.5 to 3:1. The reaction is carried out at a reduced temperature of from −70° to about 0°, preferably from about −45° to about −30°.

After the initial reaction with phosphorous oxychloride and dimethylformamide has taken place, the reaction mixture is treated with an excess of tertiary organic amine. Suitable tertiary amines that may be mentioned are triethylamine, pyridine, N-methylpiperidine, and so forth. Triethylamine is particularly preferred.

The addition of the amine is normally carried out at about the same reaction temperature as for the first stage of the reaction; and then the reaction mixture is allowed to warm up to about room temperature for workup.

In addition to the formation of the desired compound of formula VIII there is formed, in varying quantities depending upon the reaction conditions and the reagents chosen, an aldehyde of the formula:

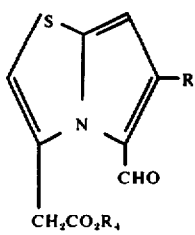

(IX)

wherein R and R₄ are as above.

The aldehyde of formula IX may be converted to the desired cyclized compound of formula VIII in a one step procedure by which the aldehyde is treated with an excess of pentamethylsilazane in the presence of a tertiary organic amine and a catalytic amount of a strong acid.

Suitable tertiary organic amines include triethylamine, pyridine, N-methylpiperidine and so forth. Suitable strong acids that may be utilized as catalysts include organic sulfonic acids such as p-toluenesulfonic acid, methanesulfonic acid and the like. p-Toluenesulfonic acid is particularly preferred.

The quantity of tertiary amine utilized in the reaction will normally be in excess relative to the aldehyde, for example about a 2 to about a 10-fold molar excess.

The sulfonic acid utilized will be present in catalytic amounts for example from about 5 to about 20 mole percent relative to the aldehyde.

The conversion from compound formula IX to that of formula VIII is carried out by heating the mixture of reagents in an inert organic solvent. The temperature of the reaction may be from about 35 to about 80° preferably from about 50 to about 70°.

Suitable inert organic solvents that may be utilized include organic ethers such as, diethylether, tetrahydrofuran, dioxane, ethylene glycol dimethylether, and the like. A particularly preferred solvent is tetrahydrofuran.

In the final reaction step the ester of formula VIII is converted to the free acid of formula I by standard saponification procedures. For example, the compound of formula VIII may be treated with excess alkali metal hydroxide, i.e. sodium hydroxide in aqueous alcoholic solution at an elevated temperature, preferably at the reflux point of the reaction medium. The acid of formula I is isolated by standard extraction techniques after acidification of the reaction mixture. According to this procedure there may be prepared the following compounds of formula I:

3-carboxy-5-(3-chlorophenyl)thiacycl[2.2.2]azine,
3-carboxy-5-(4-chlorophenyl)thiacycl[2.2.2]azine,
3-carboxy-5-(3-fluorophenyl)thiacycl[2.2.2]azine,
3-carboxy-5-(4-fluorophenyl)thiacycl[2.2.2]azine,
3-carboxy-5-(3-methylphenyl)thiacycl[2.2.2]azine,
3-carboxy-5-(4-methylphenyl)thiacycl[2.2.2]azine,
3-carboxy-5-(3-ethylphenyl)thiacycl[2.2.2]azine,
3-carboxy-5-(4-ethylphenyl)thiacycl[2.2.2]azine,
3-carboxy-5-(3-propylphenyl)thiacycl[2.2.2]azine,
3-carboxy-5-(4-propylphenyl)thiacycl[2.2.2]azine,
3-carboxy-5-(3-isopropylphenyl)thiacycl[2.2.2]azine,
3-carboxy-5-(4-isopropylphenyl)thiacycl[2.2.2]azine,
3-carboxy-5-(3-butylphenyl)thiacycl[2.2.2]azine,
3-carboxy-5-(4-butylphenyl)thiacycl[2.2.2]azine,
3-carboxy-5-(3-isobutylphenyl)thiacycl[2.2.2]azine,
3-carboxy-5-(4-isobutylphenyl)thiacycl[2.2.2]azine,
3-carboxy-5-(3-sec-butylphenyl)thiacycl[2.2.2]azine,
3-carboxy-5-(4-sec-butylphenyl)thiacycl[2.2.2]azine,
3-carboxy-5-(3-tert-butylphenyl)thiacycl[2.2.2]azine,
3-carboxy-5-(4-tert-butylphenyl)thiacycl[2.2.2]azine, 3-carboxy-5-(3-methoxyphenyl)thiacycl[2.2.2]azine,
3-carboxy-5-(4-methoxyphenyl)thiacycl[2.2.2]azine,
3-carboxy-5-(3-ethoxyphenyl)thiacycl[2.2.2]azine,
3-carboxy-5-(4-ethoxyphenyl)thiacycl[2.2.2]azine,
3-carboxy-5-(3-propoxyphenyl)thiacycl[2.2.2]azine,
3-carboxy-5-(4-propoxyphenyl)thiacycl[2.2.2]azine,
3-carboxy-5-(3-isopropoxyphenyl)thiacycl[2.2.2]azine,
3-carboxy-5-(4-isopropoxyphenyl)thiacycl[2.2.2]azine,
3-carboxy-5-(3-butoxyphenyl)thiacyl[2.2.2]azine,
3-carboxy-5-(4-butoxyphenyl)thiacycl[2.2.2]azine,
3-carboxy-5-(3-isobutoxyphenyl)thiacycl[2.2.2]azine,
3-carboxy-5-(4-isobutoxyphenyl)thiacycl[2.2.2]azine,
3-carboxy-5-(3-sec-butoxyphenyl)thiacycl[2.2.2]azine,
3-carboxy-5-(4-sec-butoxyphenyl)thiacycl[2.2.2]azine,
3-carboxy-5-(3-tert-butoxyphenyl)thiacycl[2.2.2]azine,
3-carboxy-5-(4-tert-butoxyphenyl)thiacycl[2.2.2]azine, A particularly preferred compound of formula I is 3-carboxy-5-phenylthiacycl[2.2.2]azine.

The free acids of formula I may be converted to a large variety of esters represented by the formula:

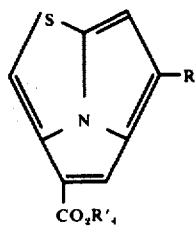

(VIIIa)

wherein R is as above and $R_4'$ is lower alkyl, phenyl or phenyllower alkyl, by esterification methods known per se. Among the types of esters which may be prepared are methyl, ethyl, propyl, butyl, tert-butyl, hexyl, octyl, phenyl, benzyl, 2-phenylethyl, 4-phenylbutyl, and so forth. These esters may be prepared by methods known per se such as, for example, Fischer esterification, reaction with a diazoalkane reagent or reacting with an alcohol and trifluoroacetic anhydride.

These esters may, of course, be saponified in the usual manner to afford the acids of formula I, if desired. The acids of formula I may be converted to their pharmaceutically acceptable salts by conventional techniques by reacting with pharmaceutically acceptable non-toxic bases, as described above.

The practice of the present invention will become more apparent by reference to the following illustrative preparations and examples, by which there are illustrated specific embodiments of the novel compounds and processes. It should be recognized by those skilled in the art that the descriptions contained herein are illustrative only of the invention and should not be construed as limiting the scope or spirit of the invention in any manner.

PREPARATION OF STARTING MATERIALS AND EXAMPLES

Preparation 1

2-Methyl-4-carboethoxymethylthiazole is prepared according to the method of Steude (Ann, 261, p.22) and Arakawa et al. (*Chem. Pharm. Bull*, 20, p. 1041).

Preparation 2

Phenacyl bromide is known. Substituted phenacyl bromides are prepared according to the following general procedure, illustrated by the preparation of 4-methoxyphenacyl bromide. The products may be purified by recrystallization or simple column chromatography. Benzoic acids having a m- or p- alkoxy substituent of from 2-4 carbon atoms which are not known, may be prepared from the corresponding hydroxybenzoic acid esters according to the procedure in preparation 3, infra. 15.2G of 4-methoxybenzoic acid is refluxed in 30 ml. of thionyl chloride containing 0.2 ml. of dimethylformamide for 4 hours. The solution is evaporated and the residue dissolved in toluene and evaporated. Dissolution of the residue in toluene and evaporation is repeated a second time. The residue is dissolved in ether and added dropwise to an ether solution of 0.3 moles of diazomethane at 0° with vigorous stirring. After 30 minutes, the ether solution is saturated with anhydrous hydrogen bromide; then washed with dilute sodium bicarbonate, dried, and evaporated to give 4'-methoxy phenacyl bromide, m.p. 69°–71°.

Following the above procedure, and replacing 4-methoxybenzoic acid with the appropriately substituted benzoic acids, there may be prepared the following phenacyl bromides:
3'-chlorophenacyl bromide
4'-chlorophenacyl bromide
3'-fluorophenacyl bromide
4'-fluorophenacyl bromide
3'-methylphenacyl bromide
4'-methylphenacyl bromide
3'-ethylphenacyl bromide
4'-ethylphenacyl bromide
3'-propylphenacyl bromide
4'-propylphenacyl bromide
3'-isopropylphenacyl bromide
4'-isopropylphenacyl bromide
3'-butylphenacyl bromide
4'-butylphenacyl bromide
3'-isobutylphenacyl bromide
4'-isobutylphenacyl bromide
3'-sec-butylphenacyl bromide
4'-sec-butylphenacyl bromide
3'-tert-butylphenacyl bromide
4'-tert-butylphenacyl bromide
3'-methoxyphenacyl bromide
3'-ethoxyphenacyl bromide
4'-ethoxyphenacyl bromide
3'-propoxyphenacyl bromide
4'-propoxyphenacyl bromide
3'-isopropoxyphenacyl bromide
4'-isopropoxyphenacyl bromide
3'-butoxyphenacyl bromides
4'-butoxyphenacyl bromides
3'-isobutoxyphenacyl bromides
4-isobutoxyphenacyl bromides
3'-sec-butoxyphenacyl bromides
4'-sec-butoxyphenacyl bromides 3'-tert-butoxyphenacyl bromides
4'-tert-butoxyphenacyl bromides

Preparation 3

3'-isobutoxyphenacyl bromide and 3'-sec-butoxyphenacyl bromide, which are not known, may be prepared according to the following procedure.

One equivalent of methyl 3'-hydroxybenzoate in 10 ml. methanol is treated with one equivalent of sodium methoxide at room temperature, then with 1.1 equivalent of sec-butylbromide or isobutylbromide. After heating at 50° the reaction is worked up in the normal manner, and any unreacted phenol is separated by extraction with base.

The methyl 3'-alkoxybenzoate is then saponified with aqueous potassium hydroxide solution in the usual manner to afford the 3-alkoxybenzoic acid, which is converted to the corresponding phenacyl bromide according to the procedure in Preparation 2.

Preparation 4

The basic ion exchange resin used in Example 2 is prepared as follows:

A column is prepared of Amberlite CG-400 100-200mesh resin, and 3 volumes of 10% sodium hydroxide solution are passed through. The column is then flushed with distilled water until the eluent is of neutral pH and gives no reaction when added to a silver nitrate solution. The resin is air dried and slurried three times with absolute methanol before use.

EXAMPLE 1

6.9 G of 2-methyl-4-carboethoxymethyl-thiazole in 12ml. of methanol containing an excess of anhydrous dimethylamine is sealed in a stainless steel bomb (ca. 30 ml. volume) and heated to approximately 90° C for 20 hours. The contents of the bomb are then evaporated and the residue purified by vacuum distillation and recrystallization from ether to give 2-methyl-4-N,N-dimethylcarboxamidomethyl thiazole, m.p. 49°–51°.

Following the above procedure, and replacing dimethylamine with the appropriate secondary amine, there may be prepared:

2-methyl-4-N,N-diethylcarboxamidomethyl thiazole
2-methyl-4-N,N-dipropylcarboxamidomethyl thiazole
2-methyl-4-(pyrrolidino-1-carbonylmethyl)thiazole,
2-methyl-4-(piperidino-1-carbonylmethyl) thiazole,
2-methyl-4-(perhydroazepino-1-carbonylmethyl) thiazole,

EXAMPLE 2

An intimate mixture of equimolar amounts of 2-methyl-4-N,N-dimethylcarboxamidomethyl thiazole and phenacyl bromide is heated under nitrogen at 110° for 20 minutes to give a glass. A solution of 2.2g of this glass in 300 ml. of methanol is purged with argon and 4 g of basic ion exchange resin (prepared as in Preparation 4) is added at room temperature. The mixture is refluxed for 30 minutes, cooled, filtered, and evaporated. The residue is chromatographed on 100g of silica gel using chloroform to give 3-N-dimethylcarboxamidomethyl-6-phenylpyrrolo[2,1-b] thiazole which may be recrystallized from ether/methanol, m.p. 152°–155°.

Following the above procedure, and replacing phenacyl bromide with a substituted phenacyl bromide prepared as in Preparation 2, there may be prepared:

3-N,N-dimethylcarboxamidomethyl-6-(3-chlorophenyl)pyrrolo[2,1-b] thiazole,
3-N,N-dimethylcarboxamidomethyl-6-(4-chlorophenyl)pyrrolo[2,1-b] thiazole,
3-N,N-dimethylcarboxamidomethyl-6-(3-fluorophenyl)pyrrolo[2,1-b] thiazole,
3-N,N-dimethylcarboxamidomethyl-6-(4-fluorophenyl)pyrrolo[2,1-b] thiazole,
3-N,N-dimethylcarboxamidomethyl-6-(3-methylphenyl)pyrrolo[2,1-b] thiazole,
3-N,N-dimethylcarboxamidomethyl-6-(4-methylphenyl)pyrrolo[2,1-b] thiazole,
3-N,N-dimethylcarboxamidomethyl-6-(3-ethylphenyl)pyrrolo[2,1-b] thiazole,
3-N,N-dimethylcarboxamidomethyl-6-(4-ethylphenyl)pyrrolo[2,1-b] thiazole,
3-N,N-dimethylcarboxamidomethyl-6-(3-propylphenyl)pyrrolo[2,1-b] thiazole,
3-N,N-dimethylcarboxamidomethyl-6-(4-propylphenyl)pyrrolo[2,1-b] thiazole,
3-N,N-dimethylcarboxamidomethyl-6-(3-isopropylphenyl)pyrrolo[2,1-b] thiazole,
3-N,N-dimethylcarboxamidomethyl-6-(4-isopropylphenyl)pyrrolo[2,1-b] thiazole,
3-N,N-dimethylcarboxamidomethyl-6-(3-butylphenyl)pyrrolo[2,1-b] thiazole,
3-N,N-dimethylcarboxamidomethyl-6-(4-butylphenyl)pyrrolo[2,1-b] thiazole,
3-N,N-dimethylcarboxamidomethyl-6-(3-isobutylphenyl)pyrrolo[2,1-b] thiazole,
3-N,N-dimethylcarboxamidomethyl-6-(4-isobutylphenyl)pyrrolo[2,1-b] thiazole,
3-N,N-dimethylcarboxamidomethyl-6-(3-sec-butylphenyl)pyrrolo[2,1-b] thiazole,
3-N,N-dimethylcarboxamidomethyl-6-(4-sec-butylphenyl)pyrrolo[2,1-b] thiazole,
3-N,N-dimethylcarboxamidomethyl-6-(3-tert-butylphenyl)pyrrolo[2,1-b] thiazole,
3-N,N-dimethylcarboxamidomethyl-6-(4-tert-butylphenyl)pyrrolo[2,1-b] thiazole,
3-N,N-dimethylcarboxamidomethyl-6-(3-methoxyphenyl)pyrrolo[2,1-b] thiazole,
3-N,N-dimethylcarboxamidomethyl-6-(4-methoxyphenyl)pyrrolo[2,1-b] thiazole,
3-N,N-dimethylcarboxamidomethyl-6-(3-ethoxyphenyl)pyrrolo[2,1-b] thiazole,
3-N,N-dimethylcarboxamidomethyl-6-(4-ethoxyphenyl)pyrrolo[2,1-b] thiazole,
3-N,N-dimethylcarboxamidomethyl-6-(3-propoxyphenyl)pyrrolo[2,1-b] thiazole,
3-N,N-dimethylcarboxamidomethyl-6-(4-propoxyphenyl)pyrrolo[2,1-b] thiazole,
3-N,N-dimethylcarboxamidomethyl-6-(3-isopropoxyphenyl)pyrrolo[2,1-b] thiazole,
3-N,N-dimethylcarboxamidomethyl-6-(4-isopropoxyphenyl)pyrrolo[2,1-b] thiazole,
3-N,N-dimethylcarboxamidomethyl-6-(3-butoxyphenyl)pyrrolo[2,1-b] thiazole,
3-N,N-dimethylcarboxamidomethyl-6-(4-butoxyphenyl)pyrrolo[2,1-b] thiazole,
3-N,N-dimethylcarboxamidomethyl-6-(3-isobutoxyphenyl)pyrrolo[2,1-b] thiazole,
3-N,N-dimethylcarboxamidomethyl-6-(4-isobutoxyphenyl)pyrrolo[2,1-b] thiazole, 3-N,N-dimethylcarboxamidomethyl-6-(3-sec-butoxyphenyl)pyrrolo[2,1-b] thiazole,
3-N,N-dimethylcarboxamidomethyl-6-(4-sec-butoxyphenyl)pyrrolo[2,1-b] thiazole,
3-N,N-dimethylcarboxamidomethyl-6-(3-tert-butoxyphenyl)pyrrolo[2,1-b] thiazole,
3-N,N-dimethylcarboxamidomethyl-6-(4-tert-butoxyphenyl)pyrrolo[2,1-b] thiazole.

Following the above procedure, and replacing 2-methyl-4-N,N-dimethylaminocarboxamidomethyl thiazole with the thiazoles prepared according to the procedure of Example 1, there may be prepared.

3-N,N-diethylcarboxamidomethyl-6-phenylpyrrolo[2,1-b] thiazole
3-N,N-dipropylcarboxamidomethyl-6-phenylpyrrolo[2,1-b] thiazole
3-(pyrrolidino-1-carbonylmethyl)-6-phenylpyrrolo[2,1-b] thiazole,
3-(piperidino-1-carbonylmethyl)-6-phenylpyrrolo[2,1-b] thiazole,
3-(perhydroazepino-1-carbonylmethyl)-6-phenylpyrrolo [2,1-b] thiazole.

Additionally, both the phenacyl bromide and thiazole moieties may be replaced in the same procedure to afford each of the m- and p-substituted phenyl products listed above in the first group having the amide moieties of the products listed above in the second group.

EXAMPLE 3

A solution of 600mg. of 3-N,N-dimethylcarboxamidomethyl-6-phenylpyrrolo[2,1-b] thiazole in 30 ml. of 1:1 ethanol:H$_2$O is flushed with nitrogen and 3g of potassium hydroxide added. The mixture is refluxed for 18 hours and then evaporated. The residue is dissolved in water, the pH adjusted to approximately 5 and the aqueous phase extracted three times with ether. Drying and evaporation gives 3-carboxymethyl-6-phenylpyrrolo[2,1-b] thiazole, which crystallizes from ether/hexane, m.p. 114°–116°. A solution of 200mg of this acid in ether is added to excess diazomethane in ether at 0°. After 5 minutes an ethereal solution of acetic acid is added to just discharge the color of the yellow solution. Washing with dilute sodium bicarbonate, drying, and evaporation gives 3-carbomethoxymethyl-6-phenylpyrrolo[2,1-b] thiazole which crystallizes from ether/hexane, m.p. 88°–89°.

Following the above procedure, and replacing the above thiazole with the appropriately substituted thiazole prepared according to the procedure in Example 2, additional acids may be prepared. By utilizing diazomethane, diazoethane or phenyldiazomethane, or by conducting a Fisher esterification with methanol, ethanol, or benzyl alcohol and a mineral acid, the methyl, ethyl and benzyl esters of the subject acid as well as of the acids listed below may be prepared:

3-carboxymethyl-6-(3-chlorophenyl)pyrrolo[2,1-b] thiazole,
3-carboxymethyl-6-(4-chlorophenyl)pyrrolo[2,1-b] thiazole,
3-carboxymethyl-6-(3-fluorophenyl)pyrrolo[2,1-b] thiazole,
3-carboxymethyl-6-(4-fluorophenyl)pyrrolo[2,1-b] thiazole,
3-carboxymethyl-6-(3-methylphenyl)pyrrolo[2,1-b] thiazole,
3-carboxymethyl-6-(4-methylphenyl)pyrrolo[2,1-b] thiazole,
3-carboxymethyl-6-(3-ethylphenyl)pyrrolo[2,1-b] thiazole,
3-carboxymethyl-6-(4-ethylphenyl)pyrrolo[2,1-b] thiazole,
3-carboxymethyl-6-(3-propylphenyl)pyrrolo[2,1-b] thiazole,
3-carboxymethyl-6-(4-propylphenyl)pyrrolo[2,1-b] thiazole,
3-carboxymethyl-6-(3-isopropylphenyl)pyrrolo[2,1-b] thiazole,
3-carboxymethyl-6-(4-isopropylphenyl)pyrrolo[2,1-b] thiazole,
3-carboxymethyl-6-(3-butylphenyl)pyrrolo[2,1-b] thiazole,
3-carboxymethyl-6-(4-butylphenyl)pyrrolo[2,1-b] thiazole,
3-carboxymethyl-6-(3-isobutylphenyl)pyrrolo[2,1-b] thiazole,
3-carboxymethyl-6-(4-isobutylphenyl)pyrrolo[2,1-b] thiazole,
3-carboxymethyl-6-(3-sec-butylphenyl)pyrrolo[2,1-b] thiazole,
3-carboxymethyl-6-(4-sec-butylphenyl)pyrrolo[2,1-b] thiazole,
3-carboxymethyl-6-(3-tert-butylphenyl)pyrrolo[2,1-b] thiazole,
3-carboxymethyl-6-(4-tert-butylphenyl)pyrrolo[2,1-b] thiazole,
3-carboxymethyl-6-(3-methoxyphenyl)pyrrolo[2,1-b] thiazole,
3-carboxymethyl-6-(4-methoxyphenyl)pyrrolo[2,1-b] thiazole,
3-carboxymethyl-6-(3-ethoxyphenyl)pyrrolo[2,1-b] thiazole,
3-carboxymethyl-6-(4-ethoxyphenyl)pyrrolo[2,1-b] thiazole,
3-carboxymethyl-6-(3-propoxyphenyl)pyrrolo[2,1-b] thiazole,
3-carboxymethyl-6-(4-propoxyphenyl)pyrrolo[2,1-b] thiazole,
3-carboxymethyl-6-(3-isopropoxyphenyl)pyrrolo[2,1-b] thiazole,
3-carboxymethyl-6-(4-isopropoxyphenyl)pyrrolo[2,1-b] thiazole,
3-carboxymethyl-6-(3-butoxyphenyl)pyrrolo[2,1-b] thiazole,
3-carboxymethyl-6-(4-butoxyphenyl)pyrrolo[2,1-b] thiazole,
3-carboxymethyl-6-(3-isobutoxyphenyl)pyrrolo[2,1-b] thiazole,
3-carboxymethyl-6-(4-isobutoxyphenyl)pyrrolo[2,1-b] thiazole,
3-carboxymethyl-6-(3-sec-butoxyphenyl)pyrrolo[2,1-b] thiazole,
3-carboxymethyl-6-(4-sec-butoxyphenyl)pyrrolo[2,1-b] thiazole,
3-carboxymethyl-6-(3-tert-butoxyphenyl)pyrrolo[2,1-b] thiazole,
3-carboxymethyl-6-(4-tert-butoxyphenyl)pyrrolo[2,1-b] thiazole,

EXAMPLE 4

A solution of 200 mg. of 3-carbomethoxymethyl-6-phenylpyrrolo[2,1-b] thiazole in 2 ml. of dimethylformamide is cooled to −40°, and 500mg of a 1:2 mixture of phosphorous oxychloride: dimethylformamide is added. The temperature of the reaction is maintained at −40° C for 30 minutes, then 2ml of triethylamine are added and the mixture allowed to warm to room temperature. After 2 hours, 2ml of 10% sodium hydroxide solution are added; the reaction mixture is diluted with water and extracted four times with ether. The combined ether extracts are diluted with hexane and washed with water. After drying and evaporation, the residue is chromatographed on 10g of silica gel. Elution with chloroform initially gives 3-carbomethoxy-5-phenylthiacycl[2.2.2]azine as a brilliant yellow material, intensely fluorescent under long wavelength ultraviolet light, which may be crystallized from hexane, m.p. 118°–120°. Continued elution with chloroform affords 3-carbomethoxymethyl-5-formyl-6-phenylpyrrolo[2,1-b] thiazole, $\delta$3.70(3H), 4.42(2H), 6.40(1H), 6.61(1H), 0.93(1H) ppm. 150 Mg. of this aldehyde is refluxed in 100ml of tetrahydrofuran with 0.5 ml. of triethylamine, 5 mg. of p-toluenesulfonic acid, and 20ml of pentamethylsilazane to give an additional amount of 3-carbomethoxy-5-phenylthiacyl[2.2.2] azine.

Following the above procedure, and replacing the above starting material with an appropriately substituted compound prepared according to the procedure in Example 3, there may be prepared 3-carbomethoxymethyl-5-formyl-6-(3-chlorophenyl)pyrrolo[2,1-b] thiazole,
3-carbomethoxymethyl-5-formyl-6-(4-chlorophenyl)pyrrolo[2,1-b] thiazole,
3-carbomethoxymethyl-5-formyl-6-(3-fluorophenyl)pyrrolo[2,1-b] thiazole,
3-carbomethoxymethyl-5-formyl-6-(4-fluorophenyl)pyrrolo[2,1-b] thiazole,
3-carbomethoxymethyl-5-formyl-6-(3-methylphenyl)pyrrolo[2,1-b] thiazole,
3-carbomethoxymethyl-5-formyl-6-(4-methylphenyl)pyrrolo[2,1-b] thiazole,
3-carbomethoxymethyl-5-formyl-6-(3-ethylphenyl)-pyrrolo[2,1-b] thiazole,
3-carbomethoxymethyl-5-formyl-6-(4-ethylphenyl)-pyrrolo[2,1-b] thiazole,
3-carbomethoxymethyl-5-formyl-6-(3-propylphenyl)pyrrolo[2,1-b] thiazole,
3-carbomethoxymethyl-5-formyl-6-(4-propylphenyl)pyrrolo[2,1-b] thiazole,
3-carbomethoxymethyl-5-formyl-6-(3-isopropylphenyl)pyrrolo[2,1-b] thiazole,
3-carbomethoxymethyl-5-formyl-6-(4-isopropylphenyl)pyrrolo[2,1-b] thiazole,
3-carbomethoxymethyl-5-formyl-6-(3-butylphenyl)-pyrrolo[2,1-b] thiazole,
3-carbomethoxymethyl-5-formyl-6-(4-butylphenyl)-pyrrolo[2,1-b] thiazole,
3-carbomethoxymethyl-5-formyl-6-(3-isobutylphenyl)pyrrolo[2,1-b] thiazole,
3-carbomethoxymethyl-5-formyl-6-(4-isobutylphenyl)pyrrolo[2,1-b] thiazole,
3-carbomethoxymethyl-5-formyl-6-(3-sec-butylphenyl)pyrrolo[2,1-b] thiazole,
3-carbomethoxymethyl-5-formyl-6-(4-sec-butylphenyl)pyrrolo[2,1-b] thiazole,
3-carbomethoxymethyl-5-formyl-6-(3-tert-butylphenyl)pyrrolo[2,1-b] thiazole,
3-carbomethoxymethyl-5-formyl-6-(4-tert-butylphenyl)pyrrolo[2,1-b] thiazole
3-carbomethoxymethyl-5-formyl-6-(3-methoxyphenyl)pyrrolo[2,1-b] thiazole,
3-carbomethoxymethyl-5-formyl-6-(4-methoxyphenyl)pyrrolo[2,1-b] thiazole,
3-carbomethoxymethyl-5-formyl-6-(3-ethoxyphenyl)pyrrolo[2,1-b] thiazole,
3-carbomethoxymethyl-5-formyl-6-(4-ethoxyphenyl)pyrrolo[2,1-b] thiazole,
3-carbomethoxymethyl-5-formyl-6-(3-propoxyphenyl)pyrrolo[2,1-b] thiazole,
3-carbomethoxymethyl-5-formyl-6-(4-propoxyphenyl)pyrrolo[2,1-b] thiazole,
3-carbomethoxymethyl-5-formyl-6-(3-isopropoxyphenyl)pyrrolo[2,1-b] thiazole,
3-carbomethoxymethyl-5-formyl-6-(4-isopropoxyphenyl)pyrrolo[2,1-b] thiazole,
3-carbomethoxymethyl-5-formyl-6-(3-butoxyphenyl)pyrrolo[2,1-b] thiazole,
3-carbomethoxymethyl-5-formyl-6-(4-butoxyphenyl)pyrrolo[2,1-b] thiazole,
3-carbomethoxymethyl-5-formyl-6-(3-isobutoxyphenyl)pyrrolo[2,1-b] thiazole,
3-carbomethoxymethyl-5-formyl-6-(4-isobutoxyphenyl)pyrrolo[2,1-b] thiazole,
3-carbomethoxymethyl-5-formyl-6-(3-sec-butoxyphenyl)pyrrolo[2,1-b] thiazole,
3-carbomethoxymethyl-5-formyl-6-(4-sec-butoxyphenyl)pyrrolo[2,1-b] thiazole,
3-carbomethoxymethyl-5-formyl-6-(3-tert-butoxyphenyl)pyrrolo[2,1-b] thiazole,
3-carbomethoxymethyl-5-formyl-6-(4-tert-butoxyphenyl)pyrrolo[2,1-b] thiazole, as well as the corresponding ethyl and benzyl esters; and 3-carbomethoxy-5-(3-chlorophenyl)thiacycl[2.2.2]azine,
3-carbomethoxy-5-(4-chlorophenyl)thiacycl[2.2.2]azine,
3-carbomethoxy-5-(3-fluorophenyl)thiacycl[2.2.2]azine
3-carbomethoxy-5-(4-fluorophenyl)thiacycl[2.2.2]azine,
3-carbomethoxy-5-(3-methylphenyl)thiacycl[2.2.2]azine,
3-carbomethoxy-5-(4-methylphenyl)thiacycl[2.2.2]azine,
3-carbomethoxy-5-(3-ethylphenyl)thiacycl[2.2.2]azine,
3-carbomethoxy-5-(4-ethylphenyl)thiacycl[2.2.2]azine,
3-carbomethoxy-5-(3-propylphenyl)thiacycl[2.2.2]azine,
3-carbomethoxy-5-(4-propylphenyl)thiacycl[2.2.2]azine,
3-carbomethoxy-5-(3-isopropylphenyl)thiacycl[2.2.2]azine,
3-carbomethoxy-5-(4-isopropylphenyl)thiacycl[2.2.2]azine,
3-carbomethoxy-5-(3-butylphenyl)thiacycl[2.2.2]azine,
3-carbomethoxy-5-(4-butylphenyl)thiacycl[2.2.2]azine,
3-carbomethoxy-5-(3-isobutylphenyl)thiacycl[2.2.2]azine,
3-carbomethoxy-5-(4-isobutylphenyl)thiacycl[2.2.2]azine,
3-carbomethoxy-5-(3-sec-butylphenyl)thiacycl[2.2.2]azine,
3-carbomethoxy-5-(4-sec-butylphenyl)thiacycl[2.2.2]azine,
3-carbomethoxy-5-(3-tert-butylphenyl)thiacycl[2.2.2]azine, 3-carbomethoxy-5-(4-tert-butylphenyl)thiacycl[2.2.2]azine,
3-carbomethoxy-5-(3-methoxyphenyl)thiacycl[2.2.2]azine,
3-carbomethoxy-5-(4-methoxyphenyl)thiacycl[2.2.2]azine,
3-carbomethoxy-5-(3-ethoxyphenyl)thiacycl[2.2.2]azine,
3-carbomethoxy-5-(4-ethoxypheny)thiacycl[2.2.2]azine,
3-carbomethoxy-5-(3-propoxyphenyl)thiacycl[2.2.2]azine,
3-carbomethoxy-5-(4-propoxyphenyl)thiacycl[2.2.2]azine,
3-carbomethoxy-5-(3-isopropoxyphenyl)thiacycl[2.2.2]azine,
3-carbomethoxy-5-(4-isopropoxyphenyl)thiacycl[2.2.2]azine,
3-carbomethoxy-5-(3-butoxyphenyl)thiacycl[2.2.2]azine,
3-carbomethoxy-5-(4-butoxyphenyl)thiacycl[2.2.2]azine,
3-carbomethoxy-5-(3-isobutoxyphenyl)thiacycl[2.2.2]azine,
3-carbomethoxy-5-(4-isobutoxyphenyl)thiacycl[2.2.2]azine,
3-carbomethoxy-5-(3-sec-butoxyphenyl)thiacycl[2.2.2]azine,
3-carbomethoxy-5-(4-sec-butoxyphenyl)thiacycl[2.2.2]azine,
3-carbomethoxy-5-(3-tert-butoxyphenyl)thiacycl[2.2.2]azine,
3-carbomethoxy-5-(4-tert-butoxyphenyl)thiacycl[2.2.2]azine,
as well as the corresponding ethyl and benzyl esters.

EXAMPLE 5

A mixture of 300 mg. of 3-carbomethoxy-5-phenylthiacycl[2.2.2]azine, in 5 ml of methanol and 10 ml of 10% aqueous sodium hydroxide is refluxed under nitrogen for 2 hours. After cooling and acidification with concentrated hydrochloric acid, the resulting yellow precipitate is extracted into chloroform. The chloroform extracts are dried, evaporated, and the residue chromatographed on 10 g of silica gel. Elution with 5% methanol/chloroform affords 3-carboxy-5-phenylthiacycl[2.2.2]azine, m.p. 180°–185° (dec.).

Following the above procedure, and replacing the starting ester with one of the esters prepared according to the procedure in Example 4, there may be prepared:
3-carboxy-5-(3-chlorophenyl)thiacycl[2.2.2]azine,
3-carboxy-5-(4-chlorophenyl)thiacycl[2.2.2]azine,
3-carboxy-5-(3-fluorophenyl)thiacycl[2.2.2]azine,
3-carboxy-5-(4-fluorophenyl)thiacycl[2.2.2]azine,
3-carboxy-5-(3-methylphenyl)thiacycl[2.2.2]azine,
3-carboxy-5-(4-methylphenyl)thiacycl[2.2.2]azine,
3-carboxy-5-(3-ethylphenyl)thiacycl[2.2.2]azine,
3-carboxy-5-(4-ethylphenyl)thiacycl[2.2.2]azine,
3-carboxy-5-(3-propylphenyl)thiacycl[2.2.2]azine,
3-carboxy-5-(4-propylphenyl)thiacycl[2.2.2]azine,
3-carboxy-5-(3-isopropylphenyl)thiacycl[2.2.2]azine,
3-carboxy-5-(4-isopropylphenyl)thiacycl[2.2.2]azine,
3-carboxy-5-(3-butylphenyl)thiacycl[2.2.2]azine,
3-carboxy-5-(4-butylphenyl)thiacycl[2.2.2]azine,
3-carboxy-5-(3-isobutylphenyl)thiacycl[2.2.2]azine,
3-carboxy-5-(4-isobutylphenyl)thiacycl[2.2.2]azine,
3-carboxy-5-(3-sec-butylphenyl)thiacycl[2.2.2]azine,
3-carboxy-5-(4-sec-butylphenyl)thiacycl[2.2.2]azine,
3-carboxy-5-(3-tert-butylphenyl)thiacycl[2.2.2]azine,
3-carboxy-5-(4-tert-butylphenyl)thiacycl[2.2.2]azine,
3-carboxy-5-(3-methoxyphenyl)thiacycl[2.2.2]azine,
3-carboxy-5-(4-methoxyphenyl)thiacycl[2.2.2]azine,
3-carboxy-5-(3-ethoxyphenyl)thiacycl[2.2.2]azine,
3-carboxy-5-(4-ethoxyphenyl)thiacycl[2.2.2]azine,
3-carboxy-5-(3-propoxyphenyl)thiacycl[2.2.2]azine,
3-carboxy-5-(4-propoxyphenyl)thiacycl[2.2.2]azine,
3-carboxy-5-(3-isopropoxyphenyl)thiacycl[2.2.2]azine,
3-carboxy-5-(4-isopropoxyphenyl)thiacycl[2.2.2]azine,
3-carboxy-5-(3-butoxyphenyl)thiacycl[2.2.2]azine,
3-carboxy-5-(4-butoxyphenyl)thiacycl[2.2.2]azine,
3-carboxy-5-(3-isobutoxyphenyl)thiacycl[2.2.2]azine,
3-carboxy-5-(4-isobutoxyphenyl)thiacycl[2.2.2]azine,
3-carboxy-5-(3-sec-butoxyphenyl)thiacycl[2.2.2]azine,
3-carboxy-5-(4-sec-butoxyphenyl)thiacycl[2.2.2]azine,
3-carboxy-5-(3-tert-butoxyphenyl)thiacycl[2.2.2]azine,
3-carboxy-5-(4-tert-butoxyphenyl)thiacycl[2.2.2]azine.

EXAMPLE 6

10.0 G of 3-carboxy-5-phenylthiacycl[2.2.2]azine was dissolved in 150 ml. aqueous methanol and was treated with 2.07 g. of sodium hydroxide in methanol. After stirring for three hours at room temperature, the mixture was evaporated to afford sodium 3-carboxy-5-phenylthiacycl[2.2.2]azine.

In a similar manner by replacing the sodium hydroxide by 2.90 g. of potassium hydroxide there may be prepared potassium 3-carboxy-5-phenylthiacycl[2.2.2]azine.

By following the above procedures, and replacing 3-carboxy-5-phenylthiacycl[2.2.2]azine with the acids prepared in Example 5, the sodium and potassium salts of each acid may be prepared.

EXAMPLE 7

To a suspension of 200 mg. of 3-carboxy-5-phenylthiacycl[2.2.2]azine in 20 ml. of benzene is added 0.5 ml. of trifluoroacetic anhydride. The mixture immediately becomes homogeneous, and 2 ml. of tert-butyl alcohol is added. After 5 minutes, the mixture is evaporated at room temperature, and the residue chromatographed on 12 g. of silica gel. Chloroform elutes 3-carbo-t-butyloxy-5-phenylthiacycl[2.2.2]azine which may be crystallized from hexane m.p. 152°–153°.

What is claimed is:
1. A compound represented by the formula

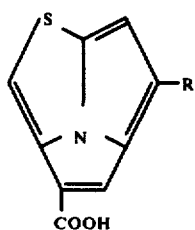

COOH

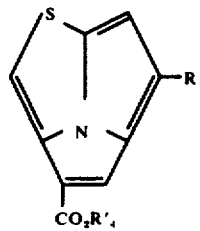

CO₂R'₄ wherein R is phenyl or phenyl monosubstituted in the meta or para position with fluoro, chloro, lower alkyl of from 1 to 4 carbon atoms or lower alkoxy of from 1 to 4 carbon atoms, and the pharmaceutically acceptable salts thereof.

2. The compound of claim 1 wherein R is phenyl, i.e. 3-carboxy-5-phenylthiacycl[2.2.2]azine, and the pharmaceutically acceptable salts thereof.

3. A compound represented by the formula wherein R is phenyl, or phenyl monosubstituted in the meta or para position with fluoro, chloro, lower alkyl of from 1 to 4 carbon atoms or lower alkoxy of from 1 to 4 carbon atoms, and $R_4'$ is lower alkyl, phenyl or phenyl lower alkyl.

4. The compound of claim 3 wherein R is phenyl.

5. The compound of claim 4 wherein $R_4'$ is methyl, i.e., 3-carbomethoxy-5-phenylthiacycl[2.2.2]azine.

6. The compound of claim 4 wherein $R_4'$ is tert-butyl, i.e. 3-carbotert-butoxy-5-phenylthiacycl[2.2.2]azine.

* * * * *